United States Patent
Tulsieram et al.

(10) Patent No.: US 6,297,056 B1
(45) Date of Patent: Oct. 2, 2001

(54) BRASSICA TRANSFORMATION VIA MICROPROJECTILE BOMBARDMENT

(75) Inventors: Lomas Tulsieram; Laurie A. Burnett; MaryAnne Arnoldo; Mai N. Le; Michael S. Bower; Katherine A. Nazarian; Christine L. Ide; Arnold Legard, all of Ontario (CA)

(73) Assignee: Pioneer Hi-Bred International, Inc., De Moines, IA (US)

( * ) Notice: Subject to any disclaimer, the term of this patent is extended or adjusted under 35 U.S.C. 154(b) by 0 days.

(21) Appl. No.: 09/416,450

(22) Filed: Oct. 12, 1999

(51) Int. Cl.[7] .............................. A01H 1/00; A01H 5/00; C12N 5/00; C12N 5/02; C12N 5/04; C12N 5/10; C12N 15/82; C12N 15/87

(52) U.S. Cl. ........................ 435/470; 800/306; 435/419; 435/420; 435/430.1; 435/470

(58) Field of Search ..................... 435/410, 419, 435/420, 430, 430.1, 440, 468, 470, 320.1; 536/23.1, 24.3, 24.33; 800/278, 293

(56) References Cited

U.S. PATENT DOCUMENTS

| | | |
|---|---|---|
| 5,188,958 | 2/1993 | Moloney et al. . |
| 5,463,174 | 10/1995 | Moloney et al. . |
| 5,750,871 | 5/1998 | Moloney et al. . |
| 6,051,756 * | 4/2000 | Chen et al. .......................... 800/293 |

FOREIGN PATENT DOCUMENTS

| | | | |
|---|---|---|---|
| WO 99/07865 * | 2/1999 | (WO) | ............................. C12N/15/82 |
| WO 99/43202 | 9/1999 | (WO) . | |

OTHER PUBLICATIONS

Chen et al. 1994. A combined use of microprojectile bombardment and DNA imbibition enhances transformation frequency of canola (*Brassica napus* L.). Theor. App. Genet. 88:187–192.*

Loh et al. 1983. Cytokinins and the regeneration of plantlets from secondary embryoids of winter oilseed rape, *Brassica napus* ssp. *oleifera*. New Phytol. vol. 95:349–358.*

Moloney et al., High Efficiency Transformation of *Bassica Napus* Using Agrobacterium Vectors, Plant Cell Reports, 1989, pp. 238–242, vol. 8.

Seki et al., Transient Expression of β–glucuronidase in *Arabidopsis thaliana* Leaves and Roots and *Brassica napus* Stems Using a Pneumatic Gun, Plant Molecular Biology, 1991, pp. 259–263, vol. 17, Kluwer Academic Publishers, Belgium.

Radke et al., Transformation and Regeneration of *Brassica rapa* Using *Agrobacterium Tumefaciens*, Plant Cell Reports, 1992, pp. 499–505, vol. 11.

Chen et al., A Combined Use of Microprojectile Bombardment and DNA Imbibition Enhances Transformation Frequency of Canola (*Brassica napus* L.), Theor. Appl. Genet, 1994, pp. 187–192, vol. 88, Canada.

Fukuoka et al., Direct Gene Delivery into Isolated Microspores of Rapeseed (*Brassica napus* L.) and the Production of Fertile Transgenic Plants, Plant Cell Reports, 1998, pp. 323–328, vol. 17,.

* cited by examiner

*Primary Examiner*—Elizabeth F. McElwain
*Assistant Examiner*—Cynthia Collins
(74) *Attorney, Agent, or Firm*—Alston & Bird LLP

(57) ABSTRACT

The invention relates to the genetic manipulation of plants, particularly plants of the genus Brassica. Methods are provided for producing transgenic Brassica plants involving the introduction of a DNA construct by microprojectile bombardment. The methods find use in the development of improved agricultural varieties of Brassica plants through the incorporation of new agronomic traits.

19 Claims, 1 Drawing Sheet

BRASSICA TRANSFORMATION VIA MICROPROJECTILE BOMBARDMENT

FIELD OF THE INVENTION

The field of the invention relates to the genetic engineering of plants, particularly methods for genetically transforming Brassica plants.

BACKGROUND OF THE INVENTION

Among the genera of cruciferous plants, the majority of the species cultivated by man are from the genus Brassica. Plants from this genus are used as a source of vegetables, condiments, vegetable oil and animal feeds. Some Brassica plants that are used for vegetable production include cabbage, cauliflower, broccoli, kale, kohlrabi, leaf mustard and rutabaga. Seeds of *B. hirta* are used to produce the popular American condiment, yellow mustard. However, on a world-wide basis, the most economically important use of Brassica species is for the production of seed-derived, vegetable oils. The predominant Brassica species grown for oil production is *B. napus*. Seeds of *B. napus* are referred to as rapeseed. Seeds of other Brassica species, particularly those grown for seed oil production, are also often referred to as rapeseed. Brassica species that are grown primarily for oil production are often called oilseed rape. In North America, canola, a type of oilseed rape that has been selected for low levels of erucic acid and glucosinolates in seeds, is the predominant Brassica plant grown for the production of vegetable oil for human consumption. While low-erucic-acid rapeseed oils, such as canola oil, may be favored for human consumption, high-erucic-acid rapeseed oils are desirable for a variety of industrial applications including the production of cosmetics, lubricants, plasticizers and surfactants.

Because of the agricultural and industrial importance of plants from the genus Brassica, plant breeders are working to develop new varieties with improved agronomic characteristics. While traditional breeding approaches are certainly important, significant improvements in cultivated Brassica varieties have been made recently through the introduction of recombinant DNA into the Brassica genome by genetic transformation methods. A number of genetically modified Brassica varieties have already reached farmers' fields in North America. Transgenic canola varieties, genetically modified for resistance to herbicides, have rapidly gained favor with agricultural producers across the canola-growing regions of the United States and Canada. The phenomenal success of the transgenic canola varieties in North America has led to an acceleration in the development of new transgenic varieties of canola. Novel, recombinant DNA-based strategies for incorporating new traits, such as disease and insect resistance, modified seed oil composition and modified seed protein composition, are being developed for canola and other Brassica species. All of the these strategies depend on genetic transformation methods to introduce the recombinant DNA into the genomes of Brassica plants.

Currently, the most favored methods for transforming Brassica species involve the use of Agrobacterium. While the Agrobacterium-based transformation methods provide a reliable means for introducing foreign DNA into dicots, there are a number of disadvantages to methods of plant transformation that involve the use of Agrobacterium. First, an undesired consequence of all Agrobacterium-based methods is the introduction of at least one T-DNA border into the genome of the recipient plant. While the T-DNA border is an essential element of the genetic mechanism by which Agrobacterium transfers DNA to a plant cell, the T-DNA border is not essential for the expression foreign genes in the recipient plant. Additionally, the accumulation of multiple T-DNA borders throughout the genome of a plant may have deleterious effects on the plant or its progeny. Second, the co-cultivation of plant tissues with Agrobacterium may slow the regeneration of a transformed plant from a transformed cell. After the co-cultivation phase, Agrobacterium must be eliminated from cultures of the plant tissues. High levels of bactericidal agents must be applied to the plant cultures to kill the Agrobacterium. While the levels of bactericidal agents applied to the cultures are generally not lethal to the plant tissues, the presence of the bactericidal agents in the cultures may negatively impact plant growth and thus, slow the regeneration of transformed plants. Third, prior to DNA transfer to a plant, natural genetic processes might occur in Agrobacterium such as genetic recombination and DNA rearrangements that may have undesired effects on the DNA fragment that is transferred to the plant. Such undesired effects may alter or eliminate the intended genetic function of the introduced DNA fragment.

Efficient Brassica transformation methods that do not involve the use of Agrobacterium are desired. While non-Agrobacterium-based, Brassica transformation methods have been reported, the efficiency of such methods, in general, has been insufficient for routine use in commercial Brassica improvement programs. To meet the increasing demands of agriculture in the world today, the pace of development of new transgenic varieties of canola and other Brassica species must be accelerated. Increasing the pace of Brassica variety development depends on the availability of reliable and efficient methods for the transformation and regeneration of transformed Brassica plants.

SUMMARY OF THE INVENTION

Methods are provided for producing transgenic Brassica plants. The methods find use in agriculture, particularly in the development of improved varieties of Brassica plants through the incorporation of new agronomic traits. The methods involve introducing a DNA construct by microprojectile bombardment into a Brassica cell that is capable of regenerating into a fertile, stably transformed Brassica plant and regenerating such a Brassica plant from the cell.

DETAILED DESCRIPTION OF THE INVENTION

Figure 1:
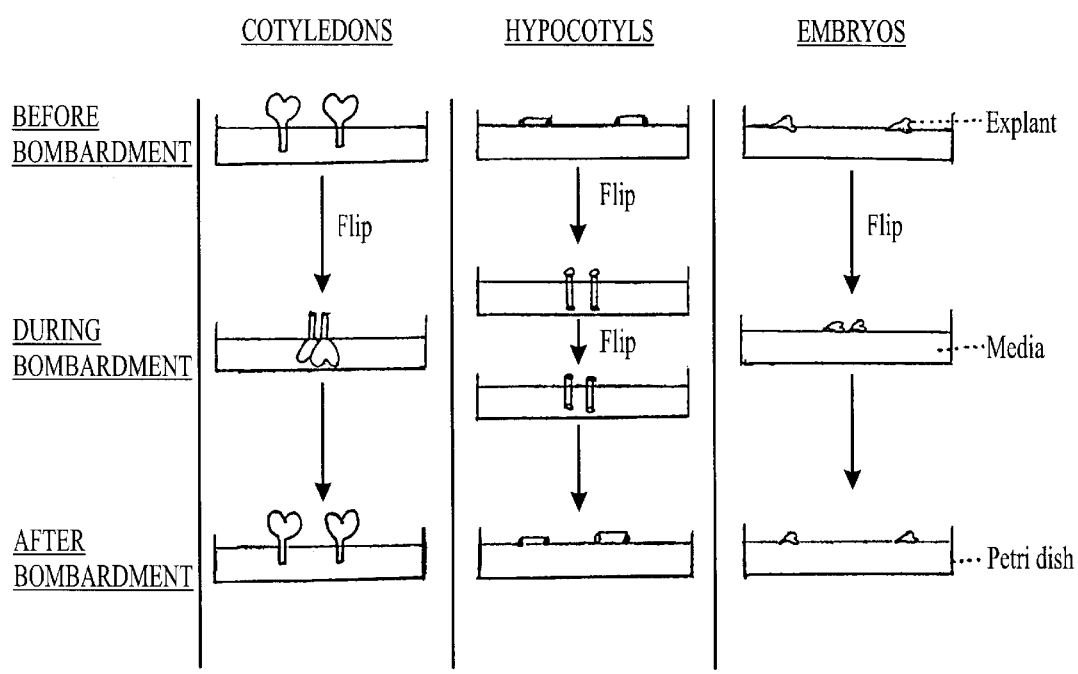
FIG. 1 is a schematic illustration of the arrangement of Brassica cotyledonary petioles (Cotyledons) with attached cotyledons, hypocotyls and embryos, before, during and after bombardment with microprojectiles coated with a DNA construct of interest.

The invention is drawn to methods for transforming Brassica plants. The methods find use in agriculture in the development of transgenic crop plants with improved agronomic characteristics. The methods find particular use in introducing new traits into a Brassica plant. Such new traits may be, for example, resistance to a herbicide, resistance to pathogens and insects, modified seed oil composition and the like. The methods involve introducing a DNA construct into the genome of a cell of a Brassica plant and regenerating a fertile, transformed plant from the cell. The present invention provides methods for transforming Brassica plants that do not depend on embryogenesis, particularly somatic embryogenesis, for the regeneration of a transformed cell into a transformed plant. The methods further involve producing a transformed plant from such an adventitious shoot.

A number of terms used herein are defined and clarified in the following section.

By "Brassica cell" is intended a cell from a Brassica plant or a cell that is produced by in vitro culture methods and is descended from a cell from a Brassica plant.

By "somatic embryo" is intended an embryo that develops from a somatic cell. The developmental process by which a somatic embryo develops from a cell is known as "somatic embryogenesis." Such a "somatic embryo" is distinct from a "zygotic embryo" which develop from a zygote.

By "microspore-derived embryo" is an embryo that develops from a microspore. Because it develops from a germ cell, such a "microspore-derived embryo" is distinct from both somatic and zygotic embryos which develop from somatic cells and zygotes, respectively.

By "cotyledonary petiole" is intended the petiole of a cotyledon or seed leaf. Such a cotyledonary petiole physically joins the lamina of a cotyledon to the shoot axis.

By "adventitious" is intended to describe an organ or other structure of a plant that does not originate in the usual location on the plant body. For example, a shoot that originated from a cotyledonary petiole is an "adventitious shoot."

By "organogenesis" is intended the developmental process wherein a cell or group of cells gives rise to an organ such as, for example, a shoot, a bud and a root.

By "chromosome doubling" is intended that each of the chromosomes in a cell is duplicated resulting in a doubling of the number of chromosomes in the cell.

By "ploidy" is intended the number of complete sets of chromosomes in the nucleus of a cell. A "haploid" cell has one set of chromosomes, and a "diploid" cell has two sets.

By "days old" is intended days after the germination of a seed was initiated. Generally, initiating germination involves providing the seed with environmental conditions which will allow the germination process to begin. The day germination is initiated is day zero. It is recognized, however, that in an agricultural setting such as, for example, a field or a plot, "days old" is generally intended as days after sowing the seed that gives rise to a plant, irrespective of environmental conditions at sowing, such as, for example, available soil moisture and soil temperature. When used in reference to the age of microspore-derived embryos, "days old" is intended as the days after placing a microspore in conditions favorably for the formation of a microspore-derived embryo.

By "effective amount" is intended an amount of an agent, compound or plant growth regulator that is capable of causing the desired effect on an organism. It is recognized that an "effective amount" may vary depending on factors, such as, for example, the organism, the target tissue of the organism, the method of administration, temperature, light, relative humidity and the like. Further, it is recognized that an "effective amount" of a particular agent may be determined by administering a range of amounts of the agent to an organism and then determining which amount or amounts cause the desired effect.

Methods are provided for transforming a Brassica plant. The methods involve transforming a Brassica cell that is capable of in vitro organogenesis with a DNA construct by microprojectile bombardment. The methods further involve regenerating the transformed cell into a transformed Brassica plant. Such a transformed Brassica plant possesses at least one copy of the DNA construct, or portion thereof, incorporated into its genome. Preferred, transformed Brassica plants of the invention are fertile, stably transformed Brassica plants. Such preferred, transformed Brassica plants are capable of producing at least one offspring that possesses at least one copy of the DNA construct of the invention, or portion thereof, stably incorporated within its genome.

Cells of the present invention may originate from any of the tissues of a Brassica plant. The tissues may be native tissues of a Brassica plant or may be Brassica tissues produced by in vitro tissue culture methods. Such in vitro-produced tissues include, but are not limited to, callus tissues and microspore-derived embryos. Methods for producing callus tissues and microspore-derived embryos are known in the art. It is recognized that both diploid and haploid tissues may be employed in the methods of the present invention. Such diploid and haploid tissues are comprised of diploid and haploid cells, respectively.

Preferred tissues of the invention are those which are capable of in vitro organogenesis. Tissues that are capable of in vitro organogenesis are comprised of at least one cell that is capable of in vitro organogenesis. More preferred tissues are from developing seeds, germinating seeds, seedlings and embryos. Most preferred tissues are from embryos, hypocotyls and cotyledonary petioles. The invention encompasses the use of whole structures, whole organs and tissues from a plant, or any part thereof. Such structures, organs, tissues and parts thereof may be excised from a plant, plant part or seed. Preferably, excision involves the use of a sharp instrument such as, for example, a scalpel, a knife or razor blade.

The DNA construct of the invention is introduced into the cell by microprojectile bombardment. Microprojectile bombardment is also known as particle bombardment, microparticle bombardment, ballistic particle acceleration and biolistic transformation. The methods of the present invention do not depend on a particular microprojectile bombardment method for introducing a DNA construct into a plant cell. Methods for introducing a DNA construct into a plant cell by microprojectile bombardment are known in the art. Generally, such methods involve applying to or coating the surface of microprojectiles with the DNA construct of interest, and then delivering the DNA-coated microparticles to the target tissue at a velocity sufficient to allow the particles to pass through cell walls and membranes and thus, enter plant cells. See, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926; all of which are herein incorporated by reference.

The methods of the invention do not depend on a particular DNA construct. Any DNA construct that may be introduced into a cell by microprojectile bombardment may be employed in the methods of the invention. Preferred DNA constructs of the invention comprise at least one nucleotide sequence of interest operably linked to a promoter that drives expression in a plant cell. More preferred DNA constructs comprise a selectable marker gene and at least one additional nucleotide sequence of interest operably linked to a promoter that drives expression in a plant cell. Most preferred DNA constructs comprise a selectable marker gene and at least one additional nucleotide sequence that is capable of conferring a desired trait on a Brassica plant.

The methods of the present invention additionally comprise regenerating the transformed cell of the invention into a fertile, stably transformed Brassica plant. Regeneration of the transformed plant involves culturing the transformed cell under conditions that result in the growth and development of the transformed cell into a transformed plant. The transformed cell and descendents thereof may develop into a transformed embryo, particularly a transformed somatic embryo which then develops into a transformed plant. Alternatively, the transformed cell and descendents thereof may develop into a transformed organ, such as, for example, an adventitious shoot, without developing into an embryo. It is recognized that regenerating a transformed Brassica plant from a transformed cell via an adventitious shoot may additionally involve the formation of callus before adventitious shoot formation. Such an adventitious shoot may be used to produce the fertile, stably transformed Brassica plant by methods known in the art. Such methods generally involve culturing an adventitious shoot in a medium and environment which favors the formation of adventitious roots on the adventitious shoot. Following root formation, the adventitious shoots may be removed from tissue culture and transferred to a substrate such as, for example, soil or other potting media, for further growth and development into a fertile, stably transformed Brassica plant.

Preferred methods of the invention involve regeneration of transformed Brassica plants from transformed adventitious shoots. Such preferred methods involve rooting adventitious shoots. Methods for rooting adventitious shoots are known in the art. The methods of the present invention do not depend on a particular method for rooting transformed Brassica shoots. Any method known in the art for rooting adventitious shoots may be employed in the methods of the present invention. Generally, rooting adventitious shoots will involve incubating shoots, for a period of time, on a medium that contains an effective amount of an auxin, such as, for example, indolebutyric acid, to induce root formation. See, for example, Moloney et al. (1989) *Plant Cell Reports* 8:238–242 and Radke et al. (1992) *Plant Cell Reports* 11:499–505; herein incorporated by reference. Rooted shoots may then be removed from culture, transferred to soil or potting medium and subjected to environmental conditions that favor growth, maturation and seed production.

It is recognized that the transformed embryos, transformed adventitious organs, and transformed plants of the invention may be chimeric. That is, such transformed embryos, organs and plants may be comprised of both transformed and non-transformed cells. It is further recognized that such chimeric plants may give rise to progeny plants that have the DNA construct of the invention, or portion thereof, stably incorporated into the genomes of all of their somatic and germ line cells.

The methods of the invention involve the transformation of cells from Brassica plants. The methods do not depend on cells of a particularly ploidy, only that such cells are capable of being transformed and regenerated into fertile, stably transformed Brassica plants. Preferred cells are diploid cells and haploid cells. While haploid cells generally do not give rise to fertile diploid plants, it is recognized that occasionally a haploid cell may spontaneous give rise to a diploid cell that is capable of developing into a fertile plant. If necessary, chromosome-doubling agents may be employed in the methods of the invention to increase the ploidy of a haploid cell two fold. That is, a haploid cell becomes a diploid cell. Such a diploid cell may give rise to a fertile, stably transformed Brassica plant. The methods of the present invention do not depend on a particular genetic mechanism of chromosome doubling. It is likely, however, that chromosome doubling results from chromosome duplication as would occur for example, during mitosis, but in the absence of cytokinesis.

Chromosome doubling of the invention involves administering an effective amount of a chromosome-doubling agent to a cell, preferably a haploid cell. Any agent that is known to increase the ploidy of cells may be employed in the methods of the invention. Chromosome-doubling agents include, but are not limited to, trifluralin, colchicine, oryzalin, amiprophosmethyl and pronamide. Depending on the desired outcome, a chromosome-doubling agent may be administered to a tissue, or a cell thereof, before, after, or both before and after, introducing a DNA construct into a cell by microprojectile bombardment. In preferred methods of the invention, an effective amount of a chromosome-doubling agent is administered after bombardment.

In a first embodiment of the invention, methods are provided for transforming a Brassica plant comprising bombarding cells from tissues of Brassica seedlings with microprojectiles coated with a DNA construct of interest. Generally, a Brassica seedling of the invention is less than about 30 days old. Preferably, the seedling tissues are derived from seedlings that were grown under aseptic conditions. Seedling tissues of the invention include, but are not limited to, petioles, cotyledonary petioles, hypocotyls, leaves, apical meristems, cotyledons, roots and the like. Preferred seedling tissues of the first embodiment are cotyledonary petioles with the attached cotyledons, and hypocotyls. While the methods of the first embodiment do not depend on seedling tissues from Brassica seedlings of any particular age, preferably, the Brassica seedlings are less than about four weeks old. More preferably, the Brassica seedlings are from about 1 to about 10 days old. Most preferably, the Brassica seedlings are from about three to about six days old.

Preferably, the seedling tissues of the first embodiment are excised from Brassica seedlings by excision with a scalpel, knife or other similar sharp-bladed instrument. For a cotyledonary petiole, the petiole is typically excised by making a cross-section through the petiole in the vicinity where the petiole attaches to the seedling shoot. If desired, the cotyledon may also be similarly removed from the petiole. However, preferred methods of the first embodiment make use of cotyledonary petioles with attached cotyledons. For a hypocotyls, hypocotyl segments may be prepared by making cross-sections through a hypocotyl. Such segments are preferably less than about 2 cm, more preferably less than about 1 cm in length, most preferably between about 4 and about 6 mm in length.

The methods of the first embodiment additionally involve bombarding the seedling tissues with microprojectiles coated with a DNA construct of interest. In preferred methods of the first embodiment, the seedling tissues are pre-incubated on a culture medium prior to bombardment. The methods of the invention do not depend on pre-incubation for any particular period of time. The duration of any pre-incubation may vary depending on factors, such as for example, the Brassica species used, the seedling tissues used, the age of the seedling tissue, the pre-incubation medium employed and environmental conditions during the pre-incubation. Preferred methods of the first embodiment involve a pre-incubation that is from less than 1 day to about 10 days in duration.

It is recognized that at the beginning of a pre-incubation, seedling tissues may be placed on, or embedded in, the pre-incubation medium in a particular orientation. It is further recognized that pre-incubation of seedling tissue in a particular orientation may favorably influence transformation and regeneration and thus result in an increased recovery of transformed Brassica plants from a transformation attempt. For cotyledonary petioles with attached cotyledons, the preferred orientation for pre-incubation is with the cut end of the petiole embedded in the medium (FIG. 1). For hypocotyls, the preferred orientation is for the longitudinal axis of the hypocotyl to be parallel to the surface of the medium (FIG. 1).

Prior to bombardment, the seedling tissues may be orientated to optimize entry of the DNA-coated microprojectiles into a particular region of the seedling tissues. For both cotyledonary petioles with attached cotyledons and hypocotyls, the preferred orientation for bombardment is with a cut end of the tissue directly facing the expected path of the DNA-coated microprojectiles and the opposite end embedded in the medium (FIG. 1). For hypocotyls, both cut ends are preferably subjected to bombardment sequentially. By bombarding both cut ends of a hypocotyl segment, increased recovery of transformed plants can be achieved due to about a two-fold increase in the number of cells bombarded per transformation attempt.

Following bombardment, the seedling tissues may also be orientated on or in the medium. For cotyledonary petioles with attached cotyledons, the preferred post-bombardment orientation is with the cut end of the petiole embedded in the medium (FIG. 1). For hypocotyls, the preferred post-bombardment orientation is for the longitudinal axis of the hypocotyl to be parallel to the surface of the medium (FIG. 1).

If the DNA construct of interest comprises a selectable marker gene, the bombarded seedling tissue may be transferred to medium containing an appropriate selective agent for that particular selectable marker gene. Such a transfer may occur immediately after bombardment or after a period of time, preferably between 0 and about 30 days after bombardment. The bombarded seedling tissues may then be monitored for the appearance of transformed adventitious shoots. Such transformed adventitious shoots may then be rooted as described supra.

In a second embodiment of the invention, methods are provided for transforming a Brassica plant comprising bombarding cells from microspore-derived embryos with microprojectiles coated with a DNA construct of interest. Methods are known in the art for producing embryos from Brassica microspores. See Fukuoka et al. (1996) *Plant Physiol.* 111:39–47 and Keller et al. (1987) *Proc. 7th Int. Rapeseed Congr.* (Plant Breeding and Acclimatization Institute, Poznan, Poland) pp. 152–157; herein incorporated by reference. Like the microspores themselves, the cells comprising such microspore-derived embryos are haploid. In the methods of the invention, whole microspore-derived embryos, or parts thereof, are bombarded with DNA-coated microprojectiles. Preferably, the microspore-derived embryos are 10 to 25 days old.

Following bombardment, the microspore-derived embryos may be transferred to a hormone-free medium for regeneration. Such hormone-free media include, but are not limited to, B5 media, MS-based media (MS salts with organics, 2% (w/v) sucrose, 0.6% (w/v) Sigma agar, pH 5.8).

However, preferred methods of the third embodiment involve secondary regeneration of the microspore-derived embryos. Such methods find use in increasing the number of transformed plants recovered from a transformation attempt. Typically, a microspore-derived embryo gives rise to a single shoot as a result of growth from the apical meristem. Secondary regeneration involves the formation of multiple shoots arising from a microspore-derived embryo. Thus, a single microspore-derived embryo can yield multiple transformed shoots from a transformation. Typically, each of the transformed shoots that arise from a single microspore-derived embryo are independent transformants. That is, each transformed shoot is derived from an independently transformed cell and thus, is genetically distinct.

Methods of secondary regeneration are known in the art. While the methods of present invention do not depend on a particular method of secondary regeneration, preferred methods involve subjecting the microspore-derived embryos to an effective amount of a cytokinin to induce secondary regeneration. Preferably, secondary regeneration is accomplished within less than about 30 days after administering a cytokinin to the microspore-derived embryos. More preferably, secondary regeneration is accomplished within less than about 10 days after administering the cytokinin. The preferred methods of secondary regeneration of the present invention may additionally involve subjecting the microspore-derived embryos to an effective amount of an auxin. In exemplary methods, an effective amount of a cytokinin is administered, with or without an effective amount of an auxin, to the microspore-derived embryos following bombardment to induce secondary regeneration.

Additionally, the methods of the second embodiment comprise administering an effective amount of a chromosome doubling agent to the microspore-derived embryos before, or preferably after, bombardment. Such chromosome-doubling agents and methods of use are described supra.

If the DNA construct utilized in methods of the second embodiment comprises a selectable marker gene, selection may be applied immediately after bombardment or after a period of time of less than 1 day to about 30 days. Selection may be applied by subjecting the microspore-derived embryos to an effective amount of an appropriate selective agent for the selectable marker gene of the DNA construct of interest. Preferably, an effective amount of the selective agent is added to the medium on which the microspore-derived embryo is cultured. The selective agent may be administered alone or in combination with one or more other compounds such as a chromosome-doubling agent or a plant growth regulator.

The methods of the present invention involve the use of plant growth regulators such as, for example, auxins and cytokinins. The plant growth regulators of the invention include, but are not limited to, both free and conjugated forms of naturally occurring plant growth regulators. Additionally, the plant growth regulators of the invention encompass synthetic analogues and precursors of such naturally occurring plant growth regulators.

Naturally occurring and synthetic analogues of auxins include, but are not limited to, indoleacetic acid (IAA), 3-indolebutyric acid (IBA), α-napthaleneacetic acid (NAA), 2,4-dichlorophenoxyacetic acid (2,4-D), 4-(2,4-dichlorophenoxy) butyric acid, 2,4,5-trichlorophenoxyacetic acid (2,4,5-T), (4-chloro-2-methylphenoxy)acetic acid (MCPA), 4-(4-chloro-2-methylphenoxy) butanoic acid (MCPB), mecoprop, diclopop, quinclorac, picloram, triclopyr, clopyralid, fluroxypyr and dicamba.

Naturally occurring and synthetic analogues of cytokinins include, but are not limited to, kinetin, zeatin, zeatin riboside, zeatin riboside phosphate, dihydrozeatin, isopentyl adenine and 6-benzyladenine.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the DNA constructs of the present invention encompass all nucleotide constructs which can be employed in the methods of the present invention for transforming Brassica plants including, but not limited to, those comprised of deoxyribonucleotides, ribonucleotides and combinations thereof. Such deoxyribonucleotides and ribonucleotides include both naturally occurring molecules and synthetic analogues. The DNA constructs of the invention also encompass all forms of nucleotide constructs including, but not limited to, single-stranded forms, double-stranded forms, hairpins, stem-and-loop structures and the like.

Furthermore, it is recognized that the methods of the invention may employ a DNA construct that is capable of directing, in a transformed plant, the expression of at least one protein, or at least one RNA, such as, for example, an rRNA, a tRNA and an antisense RNA that is complementary to at least a portion of an mRNA. Typically such a DNA construct is comprised of a coding sequence for a protein or an RNA operably linked to 5' and 3' transcriptional regulatory regions. Alternatively, it is also recognized that the methods of the invention may employ a DNA construct that is not capable of directing, in a transformed plant, the expression of a protein or RNA.

In addition, it is recognized that methods of the present invention do not depend on the incorporation of the entire DNA construct into the genome, only that the genome of the Brassica plant is altered as a result of the introduction of the DNA construct into a Brassica cell. Alterations to the genome include additions, deletions and substitution of nucleotides in the genome. While the methods of the present invention do not depend on additions, deletions, or substitutions of any particular number of nucleotides, it is recognized that such additions, deletions or substitutions comprise at least one nucleotide.

The DNA constructs of the invention also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821 and Beetham et al (1999) *Proc. Natl. Acad Sci. USA* 96:8774–8778; herein incorporated by reference.

Additionally, the term "DNA-coated microprojectiles" used herein is not intended to limit the methods of the present invention to microprojectiles coated with DNA. Rather, the term "DNA-coated microprojectiles" as used herein encompasses microprojectiles coated with any one or more of the DNA constructs of the invention as described supra.

The DNA constructs of the invention may be comprised of expression cassettes for expression in the Brassica plant of interest. The expression cassette will include 5' and 3' regulatory sequences operably linked to a gene of interest sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the gene of interest sequence to be under the transcriptional regulation of the regulatory regions. The expression cassette may additionally contain selectable marker genes.

The expression cassette will include in the 5'-3' direction of transcription, a transcriptional and translational initiation region, a gene of interest sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the gene of interest using heterologous promoters, the native promoter sequences may be used. Such constructs would change expression levels of the gene of the interest in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens,* such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92: 1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in Brassica plants.

Such constitutive promoters include, for example, the core promoter of the Rsyn7 (copending U.S. application Ser. No. 08/661,601); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297), SCP (WO 97/47756A1, WO 99/438380) and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced expression of the gene of interest within a particular plant tissue. Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad Sci. USA* 90(20):9586–9590; and Guevara-Garcia et al. (1993) *Plant J.* 4(3):495–505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. patent application Ser. No. 60/097,233, filed Aug. 20, 1998, herein incorporated by reference). For dicots, seed-specific promoters include, but are not limited to, bean β-phaseolin, napin, β-conglycinin, soybean lectin, cruciferin, and the like.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes or nucleotide sequences of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. Nos. 08/838,763, filed Apr. 10, 1997; 08/824,379, filed Mar. 26, 1997; 08/824,382, filed Mar. 26, 1997; and U.S. Pat. No. 5,703,409; herein incorporated by reference. Another example is lysine and/or sulfur rich seed protein encoded by the soybean 2S albumin described in U.S. application Ser. No. 08/618,911, filed Mar. 20, 1996, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical emasculation. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of seed is reflected in traits such as levels and types of oils, saturated and unsaturated, quality and quantity of essential amino acids, and levels of cellulose. For example, U.S. application Ser. Nos. 08/838,763 (filed Apr. 10, 1997), 08/824,379 (filed Mar. 26, 1997), and 08/824,382 (filed Mar. 26, 1997), and U.S. Pat. No. 5,703,409, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutryrate synthase), and acetoacetyl-CoA reductase (see Schubert et al. (1988) *J. Bacteriol.* 170:5837–5847) facilitate expression of polyhydroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

It is recognized that a DNA construct of the present invention may comprise an antisense construction complementary to at least a portion of a messenger RNA (mRNA) of a gene of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the complementary sequences may be used. Furthermore, portions of the antisense nucleotides may be used to disrupt the expression of the target gene. Generally, sequences of at least 50 nucleotides, 100 nucleotides, 200 nucleotides, or greater may be used. Typically, such antisense constructions will be operably linked to a promoter that drives expression in a plant.

The DNA constructs of the invention may also be employed in sense suppression methods to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.*

10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

Brassica plants of the invention include, but are not limited to, *Brassica carnata* (Ethiopian mustard), *Brassica juncea* (leaf mustard), *Brassica napus* (rape), *Brassica napus* var. *rapifera* (Swedish turnip), *Brassica nigra* (black mustard), *Brassica oleracea*, *Brassica oleracea* var. *acephala* (kale), *Brassica oleracea* var. *alboglabra* (Chinese kale), *Brassica oleracea* var. *botrytis* (cauliflower, heading broccoli), *Brassica oleracea* var. *capitata* (cabbage), *Brassica oleracea* var. *gemmifera* (Brussel sprouts), *Brassica oleracea* var. *gongylodes* (Kohlrabi), *Brassica rapa* (field mustard; also known as *Brassica campestris*), *Brassica rapa* subsp. *chinensis* (bok-choy), and *Brassica rapa* subsp. *pekinensis* (Chinese cabbage).

Preferred Brassica plants of the invention are Brassica plants are oilseed Brassica plants. Such oilseed Brassica plants are used for oil production and include but are not limited to, *Brassica juncea*, *Brassica napus* and *Brassica rapa*. More preferred Brassica plants are canola plants. Such canola plants are selections of oilseed Brassica plants (*Brassica rapa*, *Brassica napus* and *Brassica juncea*) that contain low levels of both erucic acid and glucosinolates in their seeds. The seeds of such canola plants are favored for the extraction of edible oils.

EXPERIMENTAL

EXAMPLE I

Transformation and Regeneration Using Cotyledonary Petioles

Seeds of *Brassica napus* cv. 46A65 were surface sterilized by submerging in solution of 10% commercial laundry bleach for 15 minutes, then rinsing for five minutes in sterile distilled water. The seeds were subsequently sown on GM (germination medium) at approximately 12 seeds per petri dish and allowed to germinate at 24° C. with a 16-hour photoperiod. After about four days, the cotyledons containing approximately 3 mm of the petiole were excised and placed on MMW medium, such that the petiole was submerged in the medium (FIG. 1). The plates were placed at 24° C. with a 16-hour photoperiod for preconditioning. Prior to bombardment, the cotyledons were inverted, and positioned such that the petiole ends would be in direct line with particles fired from the PDS-1000/He® apparatus (BioRad) (FIG. 1). Thirty inverted cotyledons were placed within a 5 cm diameter in the center of each MMW plate.

The DNA construct used was a supercoiled plasmid, containing CaMV 35S/PAT and SCP/GUS genes. The DNA was precipitated on 0.6, 1.0 or 1.6 $\mu$m gold particles according to the directions of the manufacturer of the PDS-1000/He® apparatus. A variety of conditions were tested which may influence the recovery of transformed Brassica plants including the number of days the cotyledonary petioles were pre-conditioned before bombardment, the bombardment pressure, the average diameter of the gold particles, the distance the plates were from the stopping plate in the apparatus and the number of days after bombardment before the cotyledonary petioles were subjected to selection. The results are summarized in Table 1.

The highest transformation efficiency was achieved in Treatment 5 in which the cotyledonary petioles were pre-conditioned for two days, bombarded at a pressure of 1100 psi using both 1.0 $\mu$m gold particles and a distance of about 9 cm from the stopping plate, and allowed four days following bombardments before selection was applied. For Treatment 5, 27 plates were bombarded, for a total of 810 cotyledons. Immediately following bombardment, the cotyledons were inverted again, such that the petioles were submerged in the MMW medium (FIG. 1). They were allowed to culture at 24° C. with a 16-hour photoperiod for 4 days. After this time, they were transferred onto MMW+Basta 2.5 mg/L to begin selection. After 3 weeks, they were re-transferred onto MMW+Basta 2.5 mg/L. When shoot regeneration occurred, green shoots were excised and transferred onto B5 medium supplemented with 4 mg/L Basta. Rooted shoots were transferred to greenhouse and analyzed by Southern hybridization analysis. Five of the rooted shoots were positive by Southern hybridization analysis. Transformation efficiency was calculated as the number of positive shoots divided by the number of cotyledonary petioles bombarded times 100. For Treatment 5, five positive shoots were identified out of 810 cotyledonary petioles bombarded for a transformation efficiency was 0.6%.

TABLE 1

Transformation of Cotyledonary Petioles

| Treatment No. | Pressure | Shelf | Particle Size | Pre-conditioning (days) | Days without selection | Selection (ppm Basta) | Transformation efficiency (%) | Progeny ratio |
|---|---|---|---|---|---|---|---|---|
| 1 | 650 | 9 | 1.6 | 0 | 4 | 2.5→4 | 0.3%(1/300) | 3:1 |
| 2 | 650 | 6 | 0.6 | 1 | 4 | 2.5→4 | 0.3%(1/300) | |
| 3 | 1100 | 9 | 0.6 | 2 | 2 | 2.5→4 | 0.1%(1/810) | |
| 4 | 1100 | 9 | 1.0 | 2 | 3 | 2.5→4 | 0.2%(2/810) | |
| 5 | 1100 | 9 | 1.0 | 2 | 4 | 2.5→4 | 0.6%(5/810) | |
| 6 | 1550 | 6 | 1.0 | 1 | 1 | 2.5→4 | 0.1%(1/810) | |
| 7 | 1550 | 6 | 1.0 | 2 | 3 | 2.5→4 | 0.2%(2/810) | |
| 8 | 1550 | 9 | 1.6 | 2 | 3 | 2.5→4 | 0.1%(1/810) | |

To demonstrate that fertile, stably transformed Brassica plants were achieved, the regenerated plant from Treatment 1 was grown to reproductive maturity and self pollinated to produce seed. The seeds were collected and germinated to give rise to progeny plants. Southern hybridization analysis of DNA extracted from tissues of 28 progeny plants revealed that 21 plants (75%) were positive for the introduced DNA construct. This corresponds to a progeny segregation ratio of 3:1 for the introduced DNA construct. The 3:1 ratio reveals that it is likely that a single copy of the DNA construct was present in the genome of the primary transformant. The results demonstrate that the primary transformant was fertile and gave rise to progeny that possessed the DNA construct in their genomes and additionally reveal that the methods disclosed herein may be used to produce fertile, stably transformed Brassica plants.

EXAMPLE II

Transformation and Regeneration Using Hypocotyl Segments

Seeds of *Brassica napus* cv 46A65 were surface sterilized and sown on GM as outlined in Example 1. After 4 days, hypocotyls were cut into 4–6 mm segments and placed horizontally on BCHI+K medium for a 2 day preconditioning period (24 C. with a 16-hour photoperiod). BCHI is a callus induction medium.

In preparation for bombardment, the hypocotyls were oriented in a vertical position, to allow the particles to enter the cut end (FIG. 1). Sixty hypocotyls were placed within a 5 cm diameter in the center of the petri dish.

The DNA construct used and the preparation procedure was that of Example I, with the exception that the DNA was precipitated on 0.6 $\mu$m gold particles. A pressure of 650 psi was used and the petri dish was placed on the top shelf (6 cm from stopping plate).

After the first bombardment, the hypocotyls were flipped, such that the opposite ends were in the uppermost position (FIG. 1). Because both cut ends are able to regenerate shoots, bombarding the second end with DNA-coated microprojectiles can increase the recovery of transformed plants per transformation attempt. Therefore, the hypocotyls were bombarded a second time to target the opposite ends. Subsequently, the hypocotyls were oriented in the horizontal position, and cultured for 7 days on BCHI+K to complete callus induction (15 explants per plate).

To induce shoot regeneration and begin selection, the hypocotyls were placed on BCH2+Basta 3.5 mg/L. The hypocotyls were transferred approximately every two weeks on fresh medium, until shoots had regenerated. Green shoots were excised and placed on B5+Basta 4 mg/L medium. Shoots were analyzed by PCR to identify potential transgenic events.

EXAMPLE III

Transformation and Regeneration Using Microspore-Derived Embryos

Microspores are immature pollen grains. Through tissue culture, microspores may be induced to develop into embryos rather than pollen. The microspore-derived embryos may also give rise to plants.

Ten- to twenty-five-day-old, microspore-derived embryos were bombarded using the parameters described supra in Example I (FIG. 1). Transient expression was achieved. In addition, microspore-derived embryos analyzed one week after bombardment had stably transformed cells. The microspore-derived embryos may be regenerated on a hormone-free medium. However, the microspore-derived embryos may also be cultured on a medium with added cytokinin (6-benzyladenine at 0.05 mg. to 0.5 mg per liter) to induce secondary regeneration. The addition of the cytokinin results in many growing points from an individual microspore-derived embryo. The selection agent is normally applied at 0–10 days after bombardment. In addition, a chemical chromosome-doubling agent, such as, for example, trifluralin, may be added to the medium to induce chromosome doubling wherein haploid transformed cells from the haploid microspore-derived embryos may be converted into transformed diploid plants. Shoots that survive on the medium containing the selective agent may be induced to form roots then potted in soil.

APPENDIX

Media Recipes

GM (Germination Medium)
    Components:
        1×MS salts and organics
        Sucrose 3%
        GelGro (gelrite 0.2%)
        pH 5.8

MMW
    Components:
        MS salts and organics
        Sucrose 3%
        BAP (4.5mg/L)
        Sigma agar #1296 (0.6%)
        pH 5.8

B5
    Components:
        B5 vitamins and minerals
        Sucrose (2%)
        Sigma agar (0.6%)
        pH 5.8

BCH1+K
    Components:
        MS salts and organics
        Sucrose 3%
        Mannitol 18 g/L
        MES 0.6 g/L
        2,4-D 1 mg/L
        Kinetin 1 mg/l
        Sigma agar #1296 (0.6%)
        pH 5.6

BCH2
    Components:
        B5 vitamins and minerals
        Sucrose (1%)
        MES 0.6 g/L
        BAP 3 mg/L
        Zeatin 1 m/L
        AgNO3 5 mg/L
        Sigma agar #1296 (0.6%)
        pH 5.6

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for transforming a Brassica plant comprising:
   (a) providing tissue from a cotyledonary petiole of a Brassica plant;
   (b) providing a DNA construct;
   (c) introducing said DNA construct into a cell from said tissue by microprojectile bombardment;
   (d) culturing said tissue so as to produce at least one transformed adventitious shoot; and
   (e) rgenerating said shoot into a fertile, stably transformed Brassica plant.

2. The method of claim 1 wherein said tissue is cultured prior to bombardment.

3. The method of claim 1 wherein said regenerating further comprises forming callus tissue.

4. The method of claim 1 wherein prior to said microprojectile bombardment said tissue is orientated to optimize entry of microprojectiles into said tissue.

5. The method of claim 1 wherein said DNA construct comprises at least one nucleotide sequence operably linked to a promoter that drives expression in a plant cell.

6. The method of claim 5 wherein said nucleotide sequence encodes a protein.

7. The method of claim 5 further comprising sense or antisense suppression.

8. The method of claim 1 wherein said DNA construct comprises: a selectable marker gene operably linked to a first promoter that drives expression in a plant cell; and a nucleotide sequence operably linked to a second promoter that drives expression in a plant cell.

9. The method of claim 8 wherein said selectable marker gene is selected from the group consisting of nptII, bar, hpt, mutant ALS genes and herbicide-resistance genes.

10. The method of claim 8 wherein said first promoter is a constitutive promoter.

11. The method of claim 10 wherein said constitutive promoter is the CaMV 35S promoter or the SCP promoter.

12. The method of claim 1 wherein said DNA construct is selected from the group consisting of chimeric vectors, chimeric mutational vectors, chimeric repair vectors, mixed-duplex oligonucleotides, self-complementary chimeric oligonucleotides and recombinogenic oligonucleobases.

13. The method of claim 12 further comprising chimeraplasty.

14. The method of claim 1, wherein said tissue from a cotyledonary petiole remains attached to the cotyledon during microprojectile bombardment.

15. The method of claim 14, wherein said tissue is excised from a Brassica seedling by making a cross-section through said cotyledonary petiole.

16. The method of claim 15 further comprising pre-incubating said tissue prior to bombardment.

17. The method of claim 16, wherein said pre-incubating comprises embedding the cut end of said tissue into a culture medium.

18. The method of claim 17 further comprising removing said cut end from said culture medium prior to said microprojectile bombardment.

19. The method of claim 18, wherein prior to said microprojectile bombardment said cut end is orientated to optimize entry of microprojectiles into said cut end.

* * * * *

UNITED STATES PATENT AND TRADEMARK OFFICE
CERTIFICATE OF CORRECTION

PATENT NO.    : 6,297,056 B1
DATED         : October 2, 2001
INVENTOR(S)   : Tulsieram et al.

It is certified that error appears in the above-identified patent and that said Letters Patent is hereby corrected as shown below:

Title page,
Item [56], References Cited, OTHER PUBLICATIONS,
Insert the following:
-- Cho et al., "Transformation of β-glucuronidase (GUS) Gene into Chinese Cabbage (*Brassica campestris* var. pekinensis) by Particle Bombardment", RDSJ. Argi Sci., 1994, pp. 181-186, Vol. 36 (2), Korea (Abstract only). --

Column 19,
Line 13, "rgenerating" should read -- regenerating --.

Signed and Sealed this

Twentieth Day of May, 2003

JAMES E. ROGAN
*Director of the United States Patent and Trademark Office*